US012723259B1

(12) United States Patent
Zhou et al.

(10) Patent No.: US 12,723,259 B1
(45) Date of Patent: Sep. 1, 2026

(54) ROOT-KNOT NEMATODE DISEASE-RELATED miRNA AND ITS REGULATORY GENE, PROTEIN AND APPLICATION

(71) Applicant: JIANGSU ACADEMY OF AGRICULTURAL SCIENCES, Nanjing (CN)

(72) Inventors: Dongmei Zhou, Nanjing (CN); Lihui Wei, Nanjing (CN); Chunting Wang, Nanjing (CN)

(73) Assignee: JIANGSU ACADEMY OF AGRICULTURAL SCIENCES, Nanjing (CN)

(*) Notice: Subject to any disclaimer, the term of this patent is extended or adjusted under 35 U.S.C. 154(b) by 674 days.

(21) Appl. No.: 18/033,664

(22) PCT Filed: Mar. 4, 2021

(86) PCT No.: PCT/CN2021/079125

§ 371 (c)(1),
(2) Date: Apr. 25, 2023

(87) PCT Pub. No.: WO2022/121127

PCT Pub. Date: Jun. 16, 2022

(30) Foreign Application Priority Data

Dec. 11, 2020 (CN) ........................ 202011459114.4

(51) Int. Cl.
*C12N 15/82* (2006.01)
*A01H 4/00* (2006.01)

(52) U.S. Cl.
CPC ......... *C12N 15/8285* (2013.01); *A01H 4/008* (2013.01); *C12N 15/8218* (2013.01)

(58) Field of Classification Search
CPC . C12N 15/8285; C12N 15/8218; A01H 4/008
See application file for complete search history.

(56) References Cited

U.S. PATENT DOCUMENTS 10,174,338 B2 * 1/2019 Carrington ......... C12N 15/8251

FOREIGN PATENT DOCUMENTS

CN 1210674 A 3/1999

OTHER PUBLICATIONS

Kravchik et al. (Published: 2014, Journal: Journal of Experimental Botany 65 (2): 725-739, 2014 doi:10.1093/jxb/ert428). (Year: 2014).*
Koonin et al. (Published: 2003, Book: Evolutionary Concept in Genetics and Genomics. In: Sequence—Evolution—Function. Springer, Boston, MA. https://doi.org/10.1007/978-1-4757-3783-7_3, pp. 1-16). (Year: 2003).*
Arazi et al. (Int. J. Mol. Sci. 2022, 23, 11979. https:// doi.org/10. 3390/ijms231911979). (Year: 2022).*
Zhao et al. (Published: 2015, Journal: Journal of Experimental Botany 66 (15) 4653-4667). (Year: 2015).*
Seppah et al. (Genes 2019, 10, 925; doi:10.3390/genes10110925 ). (Year: 2019).*
Siddique et al. (Published: 2015, Journal: PNAS 112: 41 , 12669-12674). (Year: 2015).*
Kravchik et al. (Published: 2014, Journal: Journal of Experimental Botany, 65(2):725-739, 2014 doi:10.1093/jxb/ert428 Supplementary table S6). (Year: 2014).*
China National Intellectual Property Administration, International Search Report, Application No. PCT/CN2021/079125, mailed Aug. 3, 2021, 6 pages.
Genbank “XM_004236370.4” Aug. 8, 2018, 1 page.
Ketao et al., “Identification and Characterization of microRNA during Bemisia tabaci Infestations in Solanum lycopersicum and Solanum habrochaites” Horticultureal Plant Journal, Available Mar. 7, 2018, https://doi.org/10.1016/j.hpj.2018.03.002, 11 pages.

* cited by examiner

*Primary Examiner* — David H Kruse
*Assistant Examiner* — Santosh Sharma
(74) *Attorney, Agent, or Firm* — Ziegler IP Law Group, LLC.

(57) ABSTRACT

The present application provides a root-knot nematode disease-related miRNA and its regulatory gene, proteins and application. The miRNA is miRcn1, and the genes regulated by miRcn1 include CRF9. The protein is encoded by the root-knot nematode disease-related miRNA regulatory gene provided by the present application. The application includes resistance to root-knot nematode disease. The present application experimentally confirms that miRNA miRcn1 and its target gene CRF9 have an important role in the control of root-knot nematodes. Overexpression of miRNA miRcn1 and silencing of the target gene CRF9 can improve plant resistance to root-knot nematodes.

2 Claims, 6 Drawing Sheets

Specification includes a Sequence Listing.

ROOT-KNOT NEMATODE DISEASE-RELATED miRNA AND ITS REGULATORY GENE, PROTEIN AND APPLICATION

CROSS REFERENCE TO RELATED APPLICATION(S)

This patent application is a national phase of Ser. No.: PCT/CN2021/079125 filed on Mar. 4, 2021, the entire content of which is incorporated by reference herein. This patent application claims the benefit and priority of Chinese Patent Application No. 202011459114.4 filed on Dec. 11, 2020, the disclosure of which is incorporated by reference herein in its entirety as part of the present application.

TECHNICAL FIELD

The present disclosure relates to the field of biotechnology, and in particular, to a root-knot nematode disease-related miRNA and its regulatory gene, protein and application.

BACKGROUND

Root-knot nematode (*Meloidogyne* spp.) is one of the most serious plant parasitic nematodes worldwide, causing economic losses of tens of billions of dollars every year. Among them, root-knot nematode has a wide range of hosts, which can harm hundreds of plants, causing huge economic losses after tomato and other crops are infected by it. The current control methods against this disease include chemical nematicide, corp rotation and selection of resistant varieties, however, these measures have serious limitations. Chemical nematicide has certain unsafe effects on humans and animals, and are easy to pollute the environment. Therefore, it is more and more urgent to seek new measures to control root-knot nematode disease.

In order to resist the infection of pathogens, plant has evolved a variety of complex defense mechanisms, including structural defenses, chemical defenses, allergic responses and systemic acquired resistance. Numerous studies have shown that microRNA (miRNA) play an important role in the process of PTI production in host plants in response to pathogens. Not only that, miRNA are also involved in the host's response to abiotic stress. Navarro et al. discovered for the first time that a miRNA (miR393) in *Arabidopsis* plays an important role in the process of plant disease resistance. miR393 acts on the auxin receptors TIR1, AFB2 and AFB3 mRNA to negatively regulate auxin signaling and enhance the *Arabidopsis thaliana* Resistance of mustard to *Pseudomonas syringae*. *Botrytis cinerea* infected *Arabidopsis thaliana*, down-regulated expression of miR394, over-expressed miR94, down-regulated expression of its target gene Lcr, and Lcr deletion mutant plants were more susceptible, so miR394 negatively regulated *Arabidopsis thaliana*'s response to *C. cinerea* by regulating the expression of Lcr spore resistance.

With the deepening of research, the functions of plant miRNA in the interaction between host and nematode infection have also been reported. Different miRNAs were down-regulated in *Arabidopsis thaliana*, including miR161, miR164, miR167a, miR172c, miR396c, miR396a, miR396ab, and miR398a, in order to resist the infection of beet cyst nematodes. In *Arabidopsis thaliana*, miR827 is abundantly expressed in syncytia infected by beet cyst nematodes, while its target gene NLA is down-regulated.

miR827-overexpressing plants are more susceptible, while miR827 inactivation plants are more disease-resistant. The same, overexpression of NLA increased plant resistance to nematodes, suggesting that nematodes in syncytia activate miR827 expression to suppress immune responses, promote infection and cause disease. To identify the miRNAs involved in jasmonic acid (JA)-mediated resistance to root knot nematodes in tomato, Zhao et al. constructed two miRNA libraries, wild-type (WT) and JA mutant (spr2), with a total of 263 known miRNAs and 441 new miRNAs. The expression of miR319a was significantly different. Further research showed that miR319a was down-regulated in nematode-infected or JA-treated plant tissues, and its target gene TPC4 was up-regulated. After miR319a was overexpressed, the content of JA decreased and became more sensitive. disease, and thus, miR319a is involved in tomato defense responses against root-knot nematodes. In *Arabidopsis*, overexpression of miR858 reduced the susceptibility of *Arabidopsis* to cyst nematodes, while low expression of miR858 enhanced the susceptibility of plants to nematodes. Correspondingly, transgenic plants overexpressed its target gene MYB83 were more susceptible.

Cytokinin response factors (CRFs) belong to the B-5 subgroup (subgroup VI) of the ethylene response factor (ERF) subfamily in the APETALA2/ERF superfamily, and play an important role in the interaction between plants and pathogens. In *Arabidopsis*, overexpression of CRF2 and CRF5 enhances resistance to *Pseudomonas syringae* in *Arabidopsis* (Rashotte et al., 2006; Cutcliffe et al., 2011; Kwon, 2016). In tomato, 11 CRF genes have been identified, of which, the expression of CRF9 is regulated by cytokinin. Currently, no studies have shown that CRFs are associated with root-knot nematode disease resistance.

SUMMARY

The present application overcomes the defects of the prior art and provides a root-knot nematode disease-related miRNA and its regulatory gene, protein and application.

The present application is the first to discover that CRF9 is involved in the interactions between tomato and root-knot nematodes and is regulated by miRNA miRcn1. The research results of the present application further verified the important regulatory role of miRNA in the intercropping process between nematodes and host plant, and provided a technical solution to effectively control root-knot nematode diseases by improving plant's own resistance. This technical approach can reduce the application of chemical pesticides, reduce agricultural inputs, alleviate environment pollution, and achieve efficient, safe and sustainable control of nematode diseases. It can provide a new theoretical basis for the control of nematode diseases.

In a first aspect, the present invention provides a root-knot nematode disease-related miRNA, the miRNA includes miRcn1 and genes regulated by miRcn1.

Preferably, the miRcn1 is selected from the following group:

a) base sequence shown in SEQ ID NO. 1;

b) complementary sequence of the base sequence shown in SEQ ID NO. 1; and, c) nucleotide sequence with at least 70% homology and the same function as SEQ ID NO. 1.

The SEQ ID NO. 1: taacttcgtctagctcgccttc

In a second aspect, the present invention provides a root-knot nematode disease-related miRNA regulatory gene, the gene includes CRF9.

Preferably, the CRF9 is selected from the following group:

a) base sequence shown in SEQ ID NO. 10;
b) complementary sequence of the base sequence shown in SEQ ID NO. 10; and,
c) nucleotide sequence with at least 70% homology and the same function as SEQ ID NO. 10.

The SEQ ID NO. 10:

atggatggttgcattagttcagtgaggaaagttcgcatagtttatgatgatcct-
gatgctacggactctgagagcgatgatgatcagaa tgctgctcgtttcga-
taaaaatgtgaacagaatcaagcgtgttgttaaggaaattgttat-
tcctgttgtttcatgggagaatgattttaaaaaatgttcta
aacttgataacattaggattaaagattccaagaagattcat-
gaaaataagaaggtgcagctaaaatcgaccgcgttgcctaaaggagttag-
gatg aggaaatgggggaaatatgcagct-
gagatcagagatccctcgcaggggaaaagaatatggttagggactttt
gagactgtggaggcggcttca caagcatacgaggcaaagagggct-
gaatttgataggattatttcattggggaagggtaagaattt-
gagccctggtcctgctgagtgttctatggcg tgtacgtctcatccta-
caaatgggaaaaatcgtgtgtactcacacccttccccgtcttcg
gtgctagatgtccccacatcatcagctgctgccccgg ttgagtccaat-
gaaaatctaacgagagatatggctcgaatgccagattcaggttctgaagat-
tttagcttgagttttgaggaccaaatgcttcatgaa tttatcaaacaaa-
gacagggcatttcagaattgatcgaacatcctttgatagaa
caaggctcgatcagcaatagcgttatggagatgactgaagtg aatatcag-
gaagaaaacgaaagccagacaaccaacgatagcaagttgtaaaatat-
tgacaaagggaactgaggactacagtaatgacaagtcc attttcagtgtat-
taaacgagcctacaatcatgtctcctattcatacagagctgcttc
acttgaacatcgaggaaacagcagttacggggaatagctt
gaaacttctaggctttgatgacaatgctttatttgataaagatatatcacaatt-
atttgatccatatgcagatgctatatgcttggacaacacttttcaatg ctgt-
gatggttggaatgagtgtgtttattgcaaaattttcaaagat-
gaagtcgacctagatgaagttgacttaagatggttagatgcagttttggtataa In a third aspect, the present invention provides a root-knot nematode disease-related protein, the protein is encoded by the root-knot nematode disease-related miRNA regulatory gene.

Preferably, the gene regulated by miRcn1 includes CRF9.

Preferably, the CRF9 is selected from the following group:

a) base sequence shown in SEQ ID NO. 10;
b) complementary sequence of the base sequence shown in SEQ ID NO. 10; and,
c) nucleotide sequence with at least 70% homology and the same function as SEQ ID NO. 10.

In a fourth aspect, the present invention provides an engineered bacterium, wherein, the engineered bacterium includes the root-knot nematode disease-related miRNA, and the root-knot nematode disease-related miRNA regulatory gene.

Preferably, the engineered bacterium includes *Agrobacterium tumefaciens* GV3101 transfected with the root-knot nematode disease-related miRNA and the root-knot nematode disease-related miRNA regulatory gene.

Preferably, the root-knot nematode disease-related miRNA includes miRcn1.

Preferably, the miRNA regulatory gene includes CRF9.

Preferably, the miRcn1 is selected from the following group:

a) base sequence shown in SEQ ID NO. 1;
b) complementary sequence of the base sequence shown in SEQ ID NO. 1; and,
c) nucleotide sequence with at least 70% homology and the same function as SEQ ID NO. 1.

Preferably, the CRF9 is selected from the following group:

a) base sequence shown in SEQ ID NO. 10;
b) complementary sequence of the base sequence shown in SEQ ID NO. 10; and,
c) nucleotide sequence with at least 70% homology and the same function as SEQ ID NO. 10.

In a fifth aspect, the present invention provides a plant expression vector, the plant expression vector includes the root-knot nematode disease-related miRNA, the root-knot nematode disease-related miRNA regulatory gene, 35S promoter, NOS terminator, and pEarlygate 202 vector.

Preferably, the root-knot nematode disease-related miRNA includes miRcn1.

Preferably, the miRNA regulatory gene includes CRF9.

Preferably, the miRcn1 is selected from the following group:

a) base sequence shown in SEQ ID NO. 1;
b) complementary sequence of the base sequence shown in SEQ ID NO. 1; and,
c) nucleotide sequence with at least 70% homology and the same function as SEQ ID NO. 1.

Preferably, the CRF9 is selected from the following group:

a) base sequence shown in SEQ ID NO. 10;
b) complementary sequence of the base sequence shown in SEQ ID NO. 10; and,
c) nucleotide sequence with at least 70% homology and the same function as SEQ ID NO. 10.

In a sixth aspect, the present invention provides an application of the root-knot nematode disease-related miRNA, the root-knot nematode disease-related miRNA regulatory gene, the root-knot nematode disease-related protein, the engineered bacterium, and the plant expression vector in the control of root-knot nematode disease.

Preferably, the application includes high expression of the root-knot nematode disease-related miRNA in plant for resistance to root-knot nematodes.

Preferably, the application includes knockout and/or silencing of the root-knot nematode disease-related miRNA regulatory gene in plant for resistance to root-knot nematodes.

Preferably, the root-knot nematode disease includes dicotyledonous plant root knot nematode disease. Further preferably, the root knot nematode disease includes tomato plant root nematode disease.

In a seventh aspect, the present invention provides a method of producing transgenic plant, including the following steps:

S1, transforming the root-knot nematode disease-related miRNA into plant callus, or, knockout and/or silencing of the root-knot nematode disease-related miRNA regulatory gene from plant callus, or, infecting plant callus with the engineered bacterium; and, S2, regenerating a transgenic plant from the plant callus obtained in S1.

Preferably, knockout and/or silencing of the root-knot nematode disease-related miRNA regulatory gene includes:

S11, using VIGS, CRISPR/Cas9 and gene recombination to obtain gene CRF9 knockout and/or silencing recombinant vector; and, S12, transforming the CRF9 knockout and/or silencing recombinant vector obtained in S11 into a host cell.

Preferably, the plant includes a dicotyledonous plant.

Preferably, the dicotyledonous plant includes tomato.

The present application has the following advantages over the prior art: the present application experimentally confirms that miRNA miRcn1 and its target gene CRF9 have an important role in the control of root-knot nematodes. Over-expression of miRNA miRcn1 and silencing of the target gene CRF9 can improve the resistance of plants to root-knot nematodes. Compared with the prior art, the technical solution of the present application can effectively control root-knot nematode diseases by improving plant's own resistance. The technical means can reduce the application of chemical pesticides, reduce agricultural inputs, alleviate environmental pollution, and achieve efficient, safe and sustainable control of nematode diseases.

DETAILED DESCRIPTION

Figure 1:
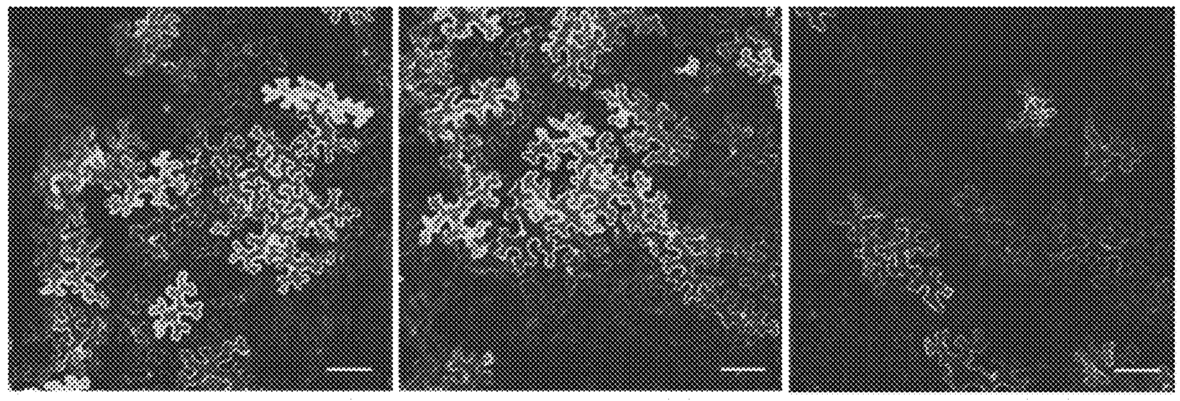
FIG. 1 shows the fluorescence plots of the three groups of miRcn1+ SlCRF9, pEarleyGate202+SlCRF9 and miR319+ SlCRF9 in embodiment 4 of the present invention.

The specific embodiments of the present invention are further described below in conjunction with the accompanying drawings and embodiments. The following embodiments are used only to illustrate the technical solutions of the invention more clearly and cannot be used to limit the scope of protection of the invention. Experimental methods for which specific conditions are not indicated in the following embodiments are selected according to the conventional methods and conditions in the art, or according to the trade description.

Embodiment 1 PCR Amplification of miRNA miRcn1 Gene and Construction of pEarleyGate202+miRcn1 Recombinant Vector 1.1 Design Primers Primers were designed by using WMD3 (www.wmd3.weigelworld.org/cgi-bin/webapp.cgi) by using the mature sequence of miRcn1, SEQ ID NO. 1(taacttcgtctagctcgccttc) and RPS300 plasmid, and 4 primer sequences were generated. The sequences were named as I miRcn1-s, II miRcn1-a, III miRcn1*s and IV miRcn1*a respectively, and were numbered as SEQ ID NO. 2, SEQ ID NO. 3, SEQ ID NO. 4 and SEQ ID NO. 5.

```
SEQ ID NO. 2 (I miRcn1-s):
gataacttcgtctagctcgccttctctctcttttgtattcc

SEQ ID NO. 3 (II miRcn1-a):
gagaaggcgagctagacgaagttatcaaagagaatcaatga

SEQ ID NO. 4 (III miRcn1*s):
gagacggcgagctagtcgaagttatcacaggtcgtgatatg

SEQ ID NO. 5 (IV miRcn1*a):
gataacttcgactagctcgccgtctctacatatatattcct
```

where, the underline part is the mature sequence of miRcn1 to obtain complementary paired sequences.

1.2 PCR Amplification of miRNA miRcn1 Gene

Two sequences located outside the pRS300 polyclonal site, SEQ ID NO.6 (CTGCAAGGCGATTAAGTTGGGTAAC) and SEQ ID NO. 7 (GCGGATAACAATTTCACACAGGAAACAG) were selected and amplified by four sets of PCR using the high fidelity enzyme Phanta Max Super-Fidelity DNA Polymerase (Vazyme) as follows.

PCR amplification 1: pRS300 was used as template, SEQ ID NO. 6 and IV miRcn1*a were used as primers for amplification, and the amplification product obtained was named as a fragment.

PCR amplification 2: pRS300 was used as template, II miRcn1-a and III miRcn1*s were used as primers for amplification, and the amplification product obtained was named as b fragment.

PCR amplification 3: pRS300 was used as template, SEQ ID NO. 7 and I miRcn1-s were used as primers for amplification, and the amplification product obtained was named as c fragment.

PCR amplification 4: a fragment obtained by PCR amplification 1, b fragment obtained by PCR amplification 2 and c fragment obtained by PCR amplification 3 were used as templates, SEQ ID NO. 6 and SEQ IN NO. 7 were used as primers to amplify the artificial fragment containing miRcn1 SEQ ID NO. 14.

```
SEQ ID NO. 14:
gaattcctgc agccccaaac acacgctcgg acgcatatta

cacatgttca tacacttaat actcgctgtt ttgaattgat

gttttaggaa tatatatgta gagacggcga gctagtcgaa

gttatcacag gtcgtgatat gattcaatta gcttccgact
```

-continued

```
cattcatcca aataccgagt cgccaaaatt caaactagac

tcgttaaatg aatgaatgat gcggtagaca aattggatca

ttgattctct ttgataactt cgtctagctc gccttctctc

tcttttgtat tccaattttc ttgattaatc tttcctgcac

aaaaacatgc ttgatccact aagtgacata tatgctgcct

tcgtatatat agttctggta aaattaacat tttgggttta

tctttattta aggcatcgcc atgggggat cc
```

1.3 Construction of pEarleyGate202+miRcn1 Recombinant Vector

The miRcn1 fragment SEQ ID NO. 14 amplified in step 1.2 was double digested with restriction endonucleases EcoRI and BamRI, the enzyme fragment was recovered from gum, ligated to the entry vector pENTRY using T4 enzyme, the ligated product was heat stimulated and transformed into *E. coli* DH5α, the transformed cells were coated on LA plates containing Kan 50 μg/ml antibiotic, and single colonies verified by PCR were incubated overnight at 37° C. in LB medium, and the plasmids were sequenced. The correctly sequenced pENTRY+miRcn1 recombinant plasmid was transferred to the expression vector pEarleyGate202 using Gateway™ LR Clonase™ II Enzyme mix (Thermo Fisher Scientific). The recombinant pEarleyGate202+miRcn1 was transformed into *E. coli* DH5α receptor cells by heat-stimulated transformation, and the transformed single colonies were verified by PCR and the plasmids were extracted for sequencing, the single colonies with correct sequencing results were cultured overnight, mixed with 50% glycerol solution 1:1 (v/v) and stored at −80° C., which is the pEarleyGate202+miRcn1 recombinant vector.

Embodiment 2 PCR Amplification of CRF9 and Construction of pEarleyGate202+CRF9 Recombinant Vector The sequence SEQ ID NO. 10 of tomato (*Solanum lycopersicum*) Moneymaker genomic cDNA was used as a template. The gene CRF9 was amplified using SEQ ID NO. 8 and SEQ ID NO. 9 as primers with the high fidelity enzyme Phanta Max Super-Fidelity DNA Polymerase (Vazyme, Nanjing, China). The sequence number of the amplification product CRF9 was SEQ ID NO. 10.

SEQ ID NO. 8: 5'-ccggaattcatggatggttgcattagttc-3'

SEQ ID NO. 9: 5'-cgcggatccttataccaaaactgcatcta-3'

```
SEQ ID NO. 10:
Atggatggttgcattagttcagtgaggaaagttcgcatagtttatgatg

atcctgatgctacggactctgagagcgatgatgatcagaatgctgctcg

tttcgataaaaatgtgaacagaatcaagcgtgttgttaaggaaattgtt

attcctgttgtttcatgggagaatgattttaaaaaatgttctaaacttg

ataacattaggattaaagattccaagaagattcatgaaaataagaaggt

gcagctaaaatcgaccgcgttgcctaaaggagttaggatgaggaaatgg

gggaaatatgcagctgagatcagagatccctcgcaggggaaaagaatat

ggttagggacttttgagactgtggaggcggcttcacaagcatacgaggc

aaagagggctgaatttgataggattatttcattggggaagggtaagaat
```

-continued

```
ttgagccctggtcctgctgagtgttctatggcgtgtacgtctcatccta

caaatgggaaaaatcgtgtgtactcacacccttccccgtcttcggtgct

agatgtccccacatcatcagctgctgccccggttgagtccaatgaaaat

ctaacgagagatatggctcgaatgccagattcaggttctgaagatttta

gcttgagttttgaggaccaaatgcttcatgaatttatcaaacaaagaca

gggcatttcagaattgatcgaacatcctttgatagaacaaggctcgatc

agcaatagcgttatggagatgactgaagtgaatatcaggaagaaaacga

aagccagacaaccaacgatagcaagttgtaaaatattgacaaagggaac

tgaggactacagtaatgacaagtccattttcagtgtattaaacgagcct

acaatcatgtctcctattcatacagagctgcttcacttgaacatcgagg

aaacagcagttacggggaatagcttgaaacttctaggctttgatgacaa

tgctttatttgataaagatatatcacaattatttgatccatatgcagat

gctatatgcttggacaacacttttcaatgctgtgatggttggaatgagt

gtgtttattgcaaaattttcaaagatgaagtcgacctagatgaagttga

cttaagatggttagatgcagttttggtataa.
```

The amplified CRF9 fragment was double digested with the restriction endonucleases EcoRI and BamHI. The reaction system was: 100 ng of CRF9 fragment, 10 μl 10× Buffer, 4 μl each of restriction endonucleases EcoRI and BamHI, and sterile water was replenished to 100 μl. The reaction system was gently mixed by pipetting and the reaction solution is incubated at 37° C. for 2-3 h. The enzyme fragments were recovered from the gum and were ligated to the introductory vector pENTRY using T4 enzyme. 1.0 μl 10×T4 DNA ligase buffer, 0.5 μl T4 DNA ligase, the fragments or vector were added in a volume calculated according to their respective concentrations, so that the amount of fragments added is about three times the amount of vector added. Then, $ddH_2O$ was replenished to 10 μl and water bath at 22° C. for 3-5 h.

The ligation production was heat-excited into *E. coli* DH5a. Centrifuge tubes with heat-transformed receptor cells were placed on ice to melt, pENTRY+CRF9 ligation product was added, pipette was gently blown and mixed, and ice bath was given for 30 min. After the ice bath, the centrifuge tubes were placed into a water bath at 42° C., heat-excited for 90 s and then quickly removed and placed on ice for 150 s. Add 800 μl of LB liquid medium and incubate for 1 h at 37° C. on a shaker with 180 rpm shaking. Centrifuge for 3 min, discard the supernatant, suck 100 μl LB liquid medium and gently blow to mix the bacterial sediment. The suspended bacterial solution was evenly coated on LA plates containing Kan 50 μg/ml antibiotics, single colonies were picked for PCR validation, incubated overnight in LB medium at 37° C., and the plasmids were extracted and sent for sequencing. Validate the correct pENTRY+CRF9 recombinant plasmid.

The pENTRY+CRF9 recombinant plasmid was transferred to the expression vector pEarleyGate202 using Gateway™ LR Clonase™ II Enzyme mix (Thermo Fisher Scientific, Waltham, USA). The reaction system was: 50-150 ng pENTRY+CRF9, 150 ng pEarleyGate202, and TE buffer was added to make up the volume to 8 μl. The reaction system was gently mixed and left on ice for 2 min, 2 μl LR Clonase™ II Enzyme mix was added and mixed, the reaction solution was placed at 25° C. for 1 h. 1 μl Proteinase K was added and mixed, the reaction solution was incubated at 37° C. for 10 min. The reaction solution was added to *E. coli* DH5a receptor cells and heat-stimulated to transform them. The transformed single colonies were verified by PCR and the plasmids were extracted for sequencing, the single colonies with correct sequencing results were cultured overnight, mixed with 50% glycerol solution 1:1 (v/v) and stored at −80° C., which is the pEarleyGate202+CRF9 recombinant vector.

Embodiment 3 Recombinant *Agrobacterium rhizogenes* GV3101+CRF9 and Recombinant *Agrobacterium rhizogenes* GV3101+miRNA miRcn1

3.1 Preparation of *Agrobacterium tumefaciens* GV3101 Receptor Cells

Activate GV3101 on solid media plates in LB [50 mg/l Rifampicin (Rif)] for 1-2 d. Single colony of GV301 was picked and inoculated in 5 ml LB (50 mg/l Rif) liquid medium at 28° C. and 200 rpm, overnight. 2 ml culture was taken into 50 ml LB liquid medium at 28° C. and 200 rpm, and continue to incubate until OD600 is about 0.5. The culture was placed on ice, ice bath at 4° C. for 30 min. The culture was centrifuged for 5 min at 5000 rpm, and the supernatant was discarded. The culture was suspended into 10 ml refrigerated 0.1 mol/1 NaCl. The culture was centrifuged for 5 min at 5000 rpm, and the supernatant was discarded. The culture was suspended into 1 ml refrigerated 20 mmol/1 $CaCl_2$), and then dispensed into 50 μl/tube (glycerol final concentration of 20%), snap freeze in liquid nitrogen and stored at −80° C.

3.2 Transformation of Recombinant *Agrobacterium rhizogenes* GV3101+CRF9 and GV3101+miRNA miRcn1 by Freeze-Thaw Method One tube of *Agrobacterium tumefaciens* GV3101 receptor cells was taken and thawed in ice bath. 3 μl expression vector plasmid of Embodiment 1 and Embodiment 2 was added into the tube, mixed gently, ice bath for 30 min, freeze in liquid nitrogen for 1 min, and water bath at 37° C. for 5 min. 950 μl antibiotic-free YEP medium was added, and then was vibrated and incubated at 28° C. and 200 rpm for 4 h. Then it was centrifuged at 10000 rpm for 1 min to concentrate the bacterial broth and the bacteriophage was back solubilized with 100 μl YEP. The re-solubilized bacterium was coated on YEP [50 mg/l Rif+50 mg/l Kan] solid medium and incubated at 28° C. for 36-48 h. Positive clones were detected by PCR of the bacterial broth. Single colonies were picked in 5 ml YEP [50 mg/l Rif+50 mg/l Kan] liquid medium, and incubated at 28° C. and 200 rpm, for 16 h in the dark to preserve the strain and extract the plasmid. The strains are *Agrobacterium rhizogenes* GV3101+CRF9 and GV3101+miRNA miRcn1.

Embodiment 4 Verify the Target Gene of miRNA miRcn1 is CRF9

Recombinant *Agrobacterium rhizogenes* GV3101+CRF9 and recombinant *Agrobacterium rhizogenes* GV3101+miRNA miRcn1 obtained in Embodiment 3 were activated overnight, transferred to LB liquid medium containing 50 mg/l Km, 25 mg/l Rif, 10 mM MES and 20 μM acetosyringone, and incubated overnight. Bacteria were collected by centrifugation and the precipitate was resuspended in buffer (10 mM $MgCl_2$, 10 mM MES, 200 μM acetosyringone) with an OD600 of about 0.8-1.0. Recombinant *Agrobacterium rhizogenes* GV3101+CRF9 suspension and recombinant *Agrobacterium rhizogenes* GV3101+miRNA miRcn1 suspension were co-injected into the leaves of Ben's tobacco grown for 6-8 weeks at a ratio of 1:1, and after 48 h, the leaves were collected and used for total protein extraction.

Plant proteins were extracted using the Plant Protein Extraction Kit (Solarbio). The method is as follows: 100-200 mg of plant tissues were taken into liquid nitrogen overnight, and the plant tissues were crushed in liquid nitrogen environment. 1 ml lysis solution was added, and the plant tissues were lysed at 4° C. for 20 min, shaking every 5 min during this period. The plant tissues were centrifuged at 4° C. and 4000 rpm for 30 min. The supernatant was aspirated into a new tube to obtain the total plant protein.

Figure 2:
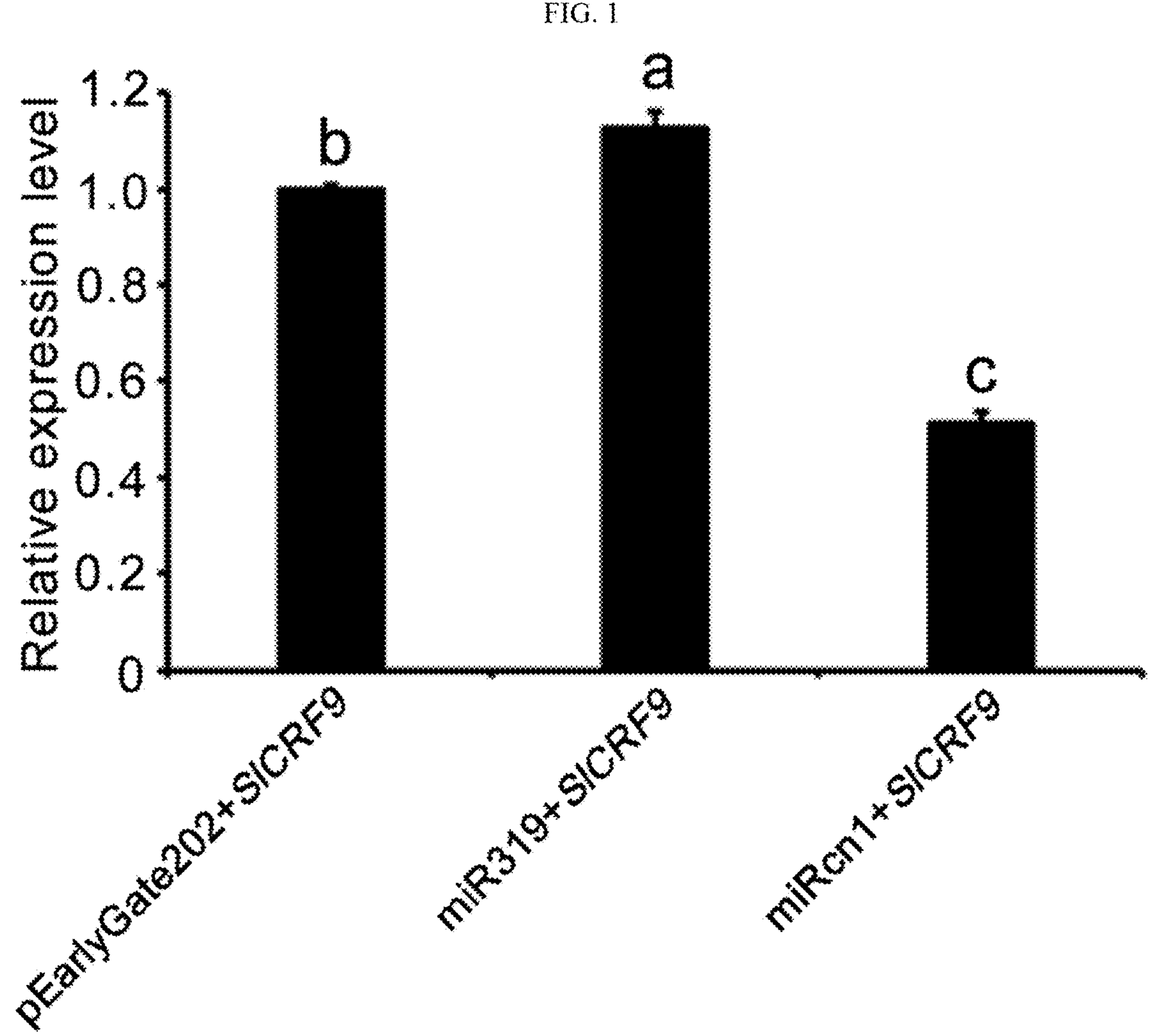
FIG. 2 shows the expression plots of the miRcn1+SlCRF9, pEarleyGate202+SlCRF9 and miR319+SlCRF9 groups in embodiment 4t of the present invention.
Figures 3, 4:
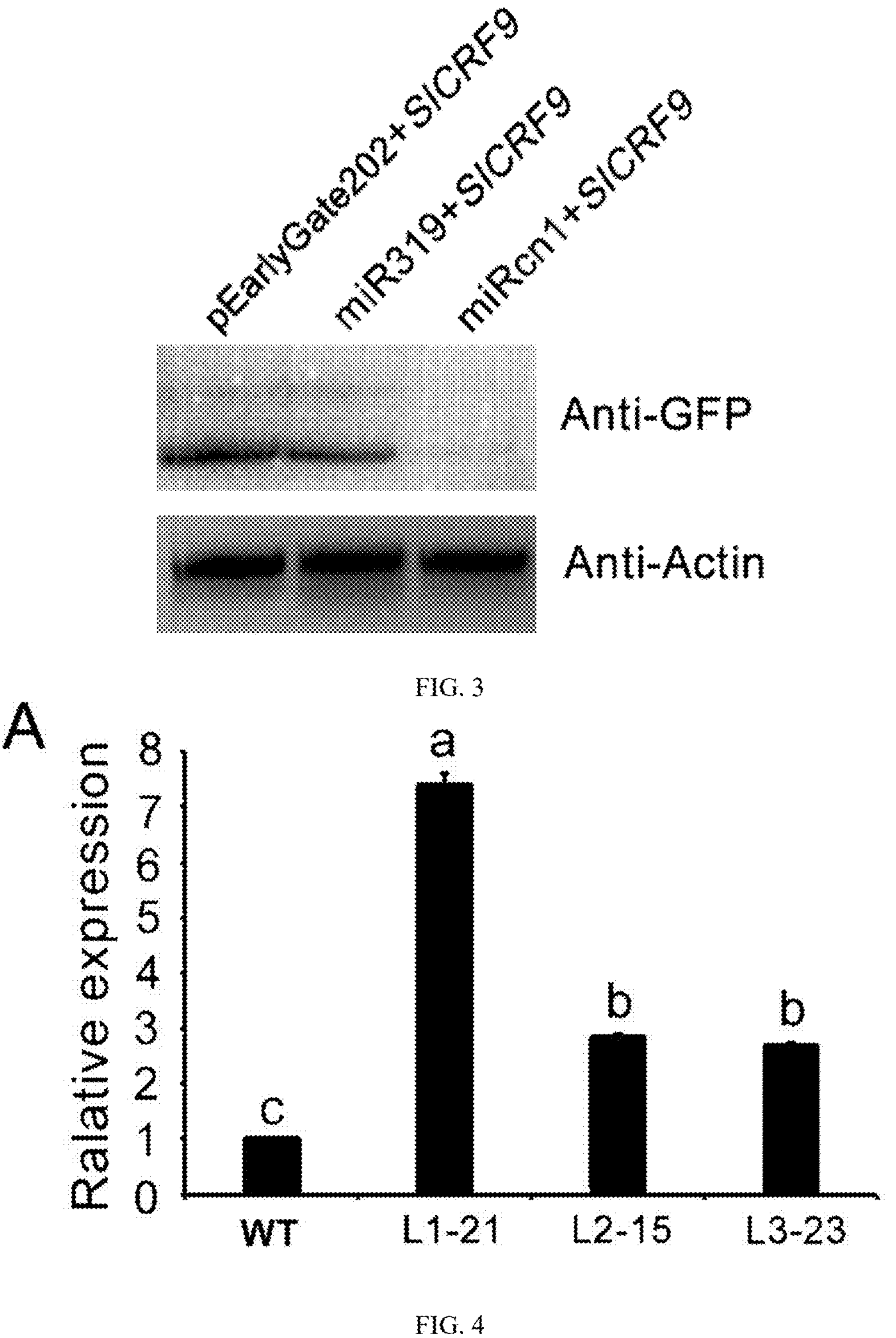
FIG. 3 is a Westernblot electrophoresis plot of the miRcn1+SlCRF9, pEarleyGate202+SlCRF9 and miR319+ SlCRF9 groups in embodiment 4 of the present invention.
FIG. 4 shows the results of miRNA miRcn1 expression assay in miRNA miRcn1 transgenic plants after root-knot nematode infection in embodiment 7 of the present invention.

Western blotting assay: The extracted proteins and collected supernatant samples were mixed with buffer, denatured at 98° C. for 10 min, added to the polyacrylamide gel loading wells, and electrophoresed at 100 V for 90 min. The proteins to be measured were transferred from the polyacrylamide gel to PVDF membrane by semi-dry transfer method. The transferred PVDF membrane was immersed in closure solution containing 5% skim milk powder and incubated on a horizontal oscillator for 1 h, then the PVDF membrane was washed 3 times with 1×TBST. The closed PVDF membrane was immersed in primary antibody incubation solution and incubated on a horizontal oscillator for 2 h, then the PVDF membrane was washed 3 times with 1×TBST. The PVDF membrane after incubation with primary antibody was immersed in secondary antibody incubation solution and incubated on a horizontal oscillator for 1 h, then the PVDF membrane was washed 3 times with 1×TBST. The PVDF membrane after incubation with secondary antibody was immersed in luminescent chromogenic solution which was prepared by using ECL Western Blotting Substrate Kit, and the results were analyzed and photographed in the imager after 5 min. The results are shown in FIG. 1-3. In the figures, SlCRF9 represents the CRF9 gene in tomato, miR319 is the control miRNA, and its target gene is PtoTCP20, which is not associated with root-knot nematode disease.

FIG. 1 shows that the fluorescence amount of miRcn1+SlCRF9 is significantly lower than that of pEarleyGate202 SlCRF9 and miR319+SlCRF9. It can be seen that miRcn1 inhibits the expression of CRF9.

FIG. 2 shows that the expression of miR319+SlCRF9 and pEarleyGate202+SlCRF9 were both higher, and were significantly higher than that of miRcn1+SlCRF9. It can be seen that miRcn1 inhibited the expression of CRF9.

FIG. 3 shows that the electrophoresis results of anti-actin (Anti-Actin) of pEarleyGate202+SlCRF9, miR319+SlCRF9 and miRcn1+SlCRF9 were almost the same, but the anti-green fluorescent protein (Anti-GFP) electropherograms had obvious bands, while the anti-green fluorescent protein (Anti-GFP) electropherograms of miRcn1+SlCRF9 had no bands. It can be seen that miRcn1 inhibited the expression of CRF9.

All of the above results indicate that miRcn1 can regulate the expression of CRF9. Specifically, miRcn1 can down-regulate the expression of CRF9.

Embodiment 5 Tomato Healing Tissue Induction and Transformation 5.1 Tomato seeds were sterilized on an ultra-clean bench. The seeds were soaked in 75% alcohol for 2 min, rinsed 3 times with sterile water, then soaked in sterilized saturated sodium phosphate for 20 min, rinsed 3 times with sterile water, then soaked in 25% (V/V) CIOROX bleach for 10 min, rinsed 7 times with sterile water, and soaked in sterile water for 8 h. Finally, the seeds were sown on 1/2 MS medium, placed in a lighted incubator and waited for germination.

5.2 About 6-8 d after tomato sowing, the seeds germinated and the cotyledons were flattened. The cotyledons were cut and soaked in MS liquid medium[MS liquid medium+0.2 mg/l 2,4-D+0.1 mg/l kinetin (KT)] for 1 h. The residual medium on the cotyledons was blotted with sterlized filter paper, the cotyledons were placed on A1 solid medium[MS liquid medium+1 mg/l indoleacetic acid (IAA)+1.75 mg/l zeatin (ZT)] and pre-cultured for 1 d.

5.3 Recombinant *Agrobacterium rhizogenes* GV3101+CRF9 and recombinant *Agrobacterium rhizogenes* GV3101+miRNA miRcn1 obtained in Embodiment 3 were inoculated in solid medium of YEB medium+500 μg/ml Strep (Strep)+50 μg/ml Rif+50 μg/ml Kan at 28° C. for 2 d. Single colonies were picked in liquid medium with 5 ml of YEB medium+500 μg/ml Strep+50 μg/ml Rif+50 μg/ml Kan and cultured at 28° C. and 200 rpm for 1.5 d in the dark. 500 μl overnight culture was added into 50 ml fresh liquid medium with YEB medium+500 μg/ml Strep+50 μg/ml Rif+50 μg/ml Kan and cultured at 28° C. and 200 rpm in the dark until OD600=1.8~2.0. Then, the bacterial was centrifuged at room temperature and 4000 rpm for 10 min and resuspended in YEB medium. The bacterial was centrifuged at room temperature and 4000 rpm for 8 min and resuspended in 40 ml MS salt medium.

5.4 The pre-cultured cotyledons were soaked in the *Agrobacterium* solution resuspended in MS salt medium for 15 min, the excess bacterial solution was blotted with sterilized filter paper, and then returned to the original medium for co-cultivation for 2 d. After 2 days of co-cultivation, the cotyledons were transferred to A2-resistant medium[MS liquid medium+1.0 μg/ml IAA+1.75 μg/ml ZT+75 μg/ml Kan+200 μg/ml Timentin (Tim)]. The cotyledons were cultured at 26° C.(16 h light)/18° C.(8 h dark). Then the medium was changed every three weeks until calluses formed.

5.5 After calluses formation, the cotyledons were transferred to A3 medium(MS liquid medium+1.0 μg/ml IAA+1.75 μg/ml ZT+75 μg/ml Kan+200 μg/ml Tim) to induce sprouting into seedlings. After the callus differentiated into growth points, the growth points were cut by a knife and transferred to A4 medium(MS liquid medium+50 μg/ml Kan+200 μg/ml Tim) for rooting screening. Positive transformed seedlings were identified and screened, which are CRF9 transgenic seedlings and miRNA miRcn1 transgenic seedlings, and then subsequent experiments were carried out.

The formula and configuration method of the above-mentioned culture medium are as follows:

| YEB medium(1 l) | |
|---|---|
| Yeast extract | 5 g |
| Peptone | 5 g |
| Beef extract | 5 g |
| $MgSO_4 \cdot 7H_2O$ | 0.5 g |
| Sucrose | 1 g |

The pH was adjusted to 7.2 with 1 M NaOH, 15 g agar was added per 1 l solid medium.

| MS medium(1 l) | |
|---|---|
| MS Powder | 4.43 g |
| Sucrose | 30 g |

The pH was adjusted to 5.9 with 1 M NaOH, 8 g agar was added per 1 l solid medium.

| 1/2 MS medium(1 l) | |
|---|---|
| MS Powder | 2.22 g |
| Sucrose | 10 g |

The pH was adjusted to 5.9 with 1 M NaOH, 8 g agar was added per 1 l solid medium.

| MS liquid medium(100 ml) | |
|---|---|
| MS Powder | 0.443 g |
| Sucrose | 3 g |
| 2,4-D (0.1 $gl^{-1}$) | 200 μl |
| KT (0.1 $gl^{-1}$) | 100 μl |

The pH was adjusted to 5.9 with 1 M NaOH.

| MS salt medium(100 ml) | |
|---|---|
| MS Salts Powder | 0.443 g |
| Sucrose | 3 g |

The pH was adjusted to 5.9 with 1 M NaOH.

| A1 medium(100 ml) | |
|---|---|
| MS solid medium | 100 ml |
| ZT (0.1 $gl^{-1}$) | 175 μl |
| IAA (0.1 $gl^{-1}$) | 100 μl |
| **A2 medium(100 ml)** | |
| MS solid medium | 100 ml |
| ZT (0.1 $gl^{-1}$) | 175 μl |
| IAA (0.1 $gl^{-1}$) | 100 μl |
| Kan (75 $gl^{-1}$) | 150 μl |
| Tim (200 $gl^{-1}$) | 100 μl |
| **A3 medium(100 ml)** | |
| MS solid medium | 100 ml |
| ZT (0.1 $gl^{-1}$) | 175 μl |
| IAA (0.1 $gl^{-1}$) | 100 μl |
| Kan (75 $gl^{-1}$) | 100 μl |
| Tim (200 $gl^{-1}$) | 100 μl |
| **A4 medium(100 ml)** | |
| MS solid medium | 100 ml |
| Kan (75 $gl^{-1}$) | 100 μl |
| Tim (200 $gl^{-1}$) | 100 μl |

Embodiment 6 Identification of Tomato Transgenic Plants

After 4 weeks of growth of GV3101+CRF9 transgenic seedlings and GV3101+miRNA miRcn1 transgenic seedlings were obtained in Embodiment 5, total RNA was extracted by using TRIzol reagent (Invitrogen) according to the method of use. 1 μg RNA was used for cDNA synthesis. cDNA was synthesized by using PrimeScript™ RT Reagent (Perfect Real Time) Kit (TaKaRa, Dalian, China). Reverse transcription follows the two-step RT-PCR procedure. The primer sequences of GV3101+miRNA miRcn1 transgenic seedlings are miRcn1-F and miRcn1-R, numbered as SEQ ID NO.11 and SEQ ID NO.12. The primer sequences of GV3101+CRF9 transgenic seedlings are CRF9-F and CRF9-R, numbered as SEQ ID NO.11 and SEQ ID NO.13. Using U6, β-tubulin and ubiquitin as controls, AceQ qPCR SYBR Green Master Mix (Vazyme, Nanjing, China) was used to analyze the expression of target genes on a fluorescent quantitative PCR instrument LightCycler 96 system (Lightcycler 96, Roche, Basel, Switzerland), 3 replicates per treatment. Plants containing the target fragment are CRF9 transgenic positive seedlings and miRNA miRcn1 transgenic seedlings positive seedlings, which can be used for subsequent experiments.

```
miRcn1-F (SEQ ID NO. 11):
5'-ctaacagaactcgccgtgaa-3'

miRcn1-R (SEQ ID NO. 12):
5'-catggcgatgccttaaataa-3',

CRF9-F (SEQ ID NO. 11):
5'-ctaacagaactcgccgtgaa-3'

CRF9-R (SEQ ID NO. 13):
5'-acgccatagaacactcagca-3'.
```

Embodiment 7 Greenhouse Pot Experiment of Root-Knot Nematode of Transgenic Plants Obtain nematodes: the tomato roots that have been infected by nematodes for more than 8 weeks were washed to remove the sediment, then were cut into pieces and placed into bottle. 10% sodium hypochlorite was added into bottle, and the bottle was shaken for 3 min. Then, the tomato roots were poured into a separation sieve in order of 20-mesh, 170-mesh and 500-mesh. After washing off the sodium hypochlorite with a large amount of water, the eggs on the 500-mesh standard sieve were collected. The collected eggs were suspended with 35% sucrose, and the upper eggs were collected. The upper eggs were added into 10% sodium hypochlorite solution for treatment, suspend for 5 min by shaking. The eggs were collected by centrifugation, and washed with sterilized water for 3 times to remove sodium hypochlorite. After aseptic incubation at room temperature for 2-3 days, the second instar larvae of *R. incognita* were collected for future use.

Nematode infection of transgenic tomato seedlings: CRF9 transgenic positive seedlings and miRNA miRcn1 transgenic seedlings positive seedlings screened in Embodiment 6 were transplanted into pots filled with fine sand and grown at 25° C. under 16 h light and 8 h dark conditions. When tomato seedlings grew to four weeks old, 500 heads of J2 suspension were inoculated. Three weeks after J2 inoculation, the number of root nodes was counted, and the number of egg masses was counted after 8 weeks. 12 seedlings per treatment were repeated 3 times.

Egg mass staining method: 100 mg briliant blue powder was weighed and dissolved in 100 ml sterilized water to prepare a mother solution. 10 ml mother solution was measured with a graduated cylinder and added into a larger beaker containing 500 ml tap water, stirred and mixed, and the solution is the working solution. The tomato roots were washed with water to remove the sandy soil. After the roots put in the working solution and dyed for 15 min, the number of egg masses were counted.

The expression levels of miRNA miRcn1 and CRF9 in the transgenic seedlings and the number of the root knots in the plants were counted and analyzed, and the results are shown in FIGS. 4-10.

FIG. 4 shows the detection results of miRNA miRcn1 expression in miRNA miRcn1 transgenic plants, wherein, WT was the control plant, L1-21, L2-15 and L3-23 were three groups of miRNA miRcn1 transgenic plants. It can be seen from FIG. 4 that the expression of miRNA miRcn1 in miRNA miRcn1 transgenic plants was significantly higher than that in the control group. It can be seen that the screened miRNA miRcn1 transgenic plants are positive plants, which can highly express miRNA miRcn1.

Figures 5, 6:
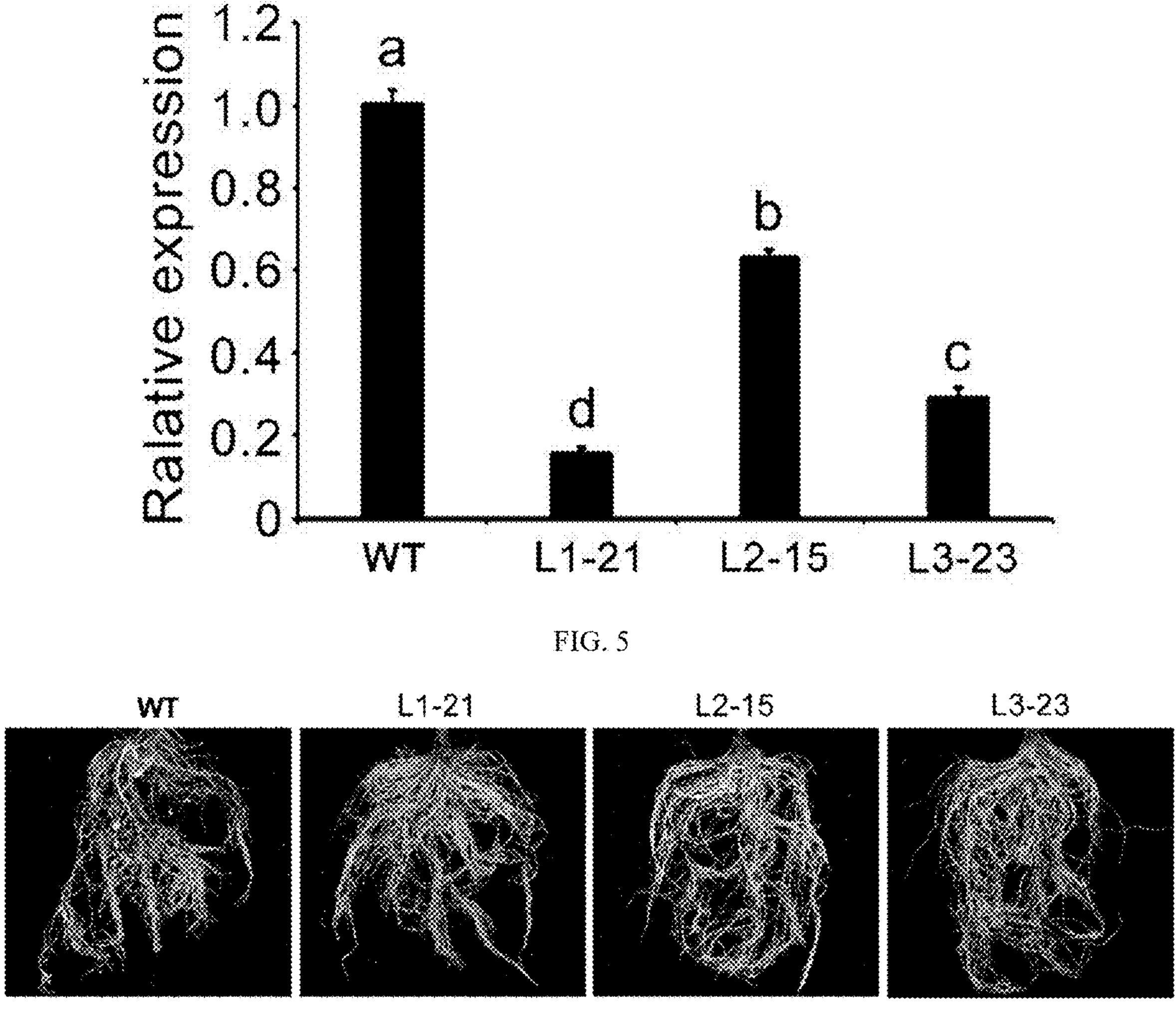
FIG. 5 shows the results of the detection of CRF9 expression in miRNA miRcn1 transgenic plants after root-knot nematode infection in embodiment 7 of the present invention.
FIG. 6 shows a root system diagram of miRNA miRcn1 transgenic plants after root-knot nematode infection in embodiment 7 of the present invention, where WT is a control plant.

FIG. 5 shows the detection results of CRF9 expression in miRNA miRcn1 transgenic plants, wherein, WT was the control plant, L1-21, L2-15 and L3-23 were three groups of miRNA miRcn1 transgenic plants. It can be seen from FIG. 5 that the expression of CRF9 in miRNA miRcn1 transgenic plants was significantly lower than that in the control group. It was further verified that the miRNA miRcn1 can down-regulate the expression of CRF9.

FIG. 6 shows the root conditions of miRNA miRcn1 transgenic plants infected with root-knot nematodes, wherein, WT was the control plant, L1-21, L2-15 and L3-23 were three groups of miRNA miRcn1 transgenic plants. It can be seen from FIG. 6 that the number of root knots of L1-21, L2-15 and L3-23 were significantly less than that of the control group. It can be seen that miRNA miRcn1 can inhibit the infection of root-knot nematodes.

Figure 7:
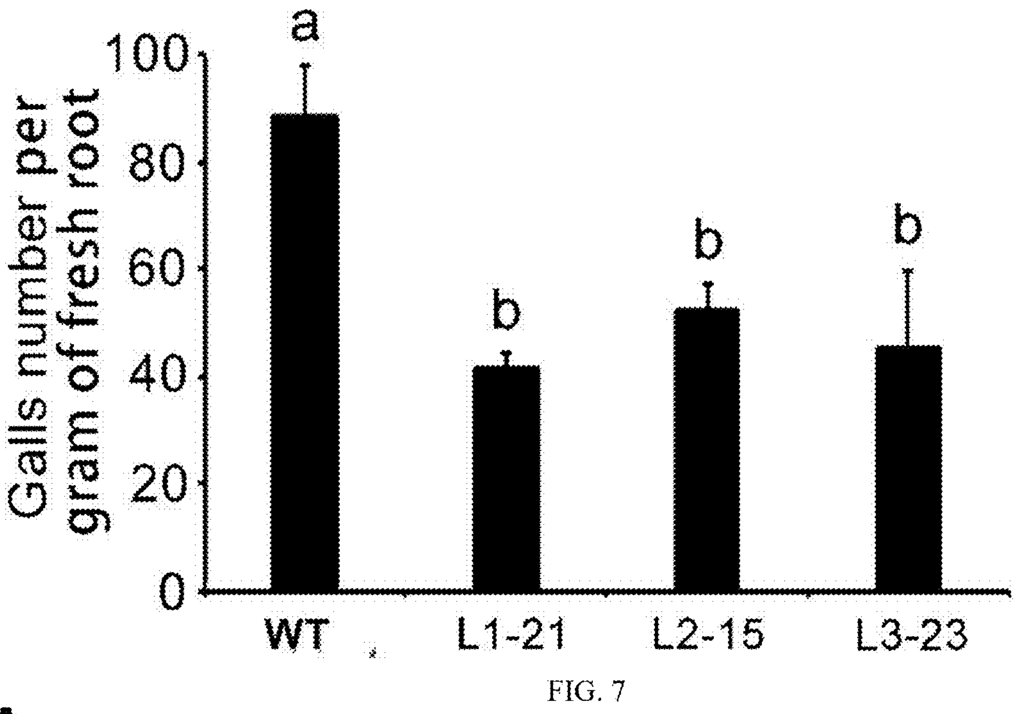
FIG. 7 shows a count of the number of root nodes of miRNA miRcn1 transgenic plants after root-knot nematode infection in embodiment 7 of the present invention.

FIG. 7 is a graph showing the number of root knots of miRNA miRcn1 transgenic plants infected with root knot nematodes, wherein, WT was the control plant, L1-21, L2-15 and L3-23 were three groups of miRNA miRcn1 transgenic plants. It can be seen from FIG. 7 that the number of root knots of L1-21, L2-15 and L3-23 were less than that of the control group. It can be seen that miRNA miRcn1 can inhibit the infection of root-knot nematodes.

Figure 8:
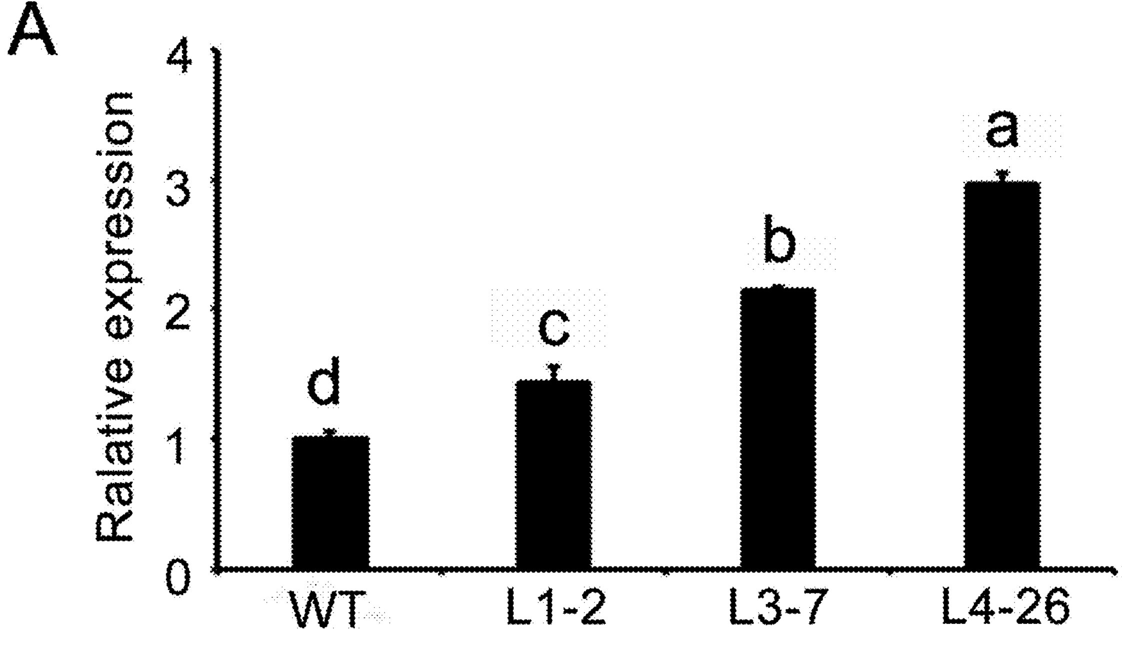
FIG. 8 shows the results of CRF9 expression assay in CRF9 transgenic plants after root-knot nematode infection in embodiment 7 of the present invention.

FIG. 8 shows the detection results of CRF9 expression in CRF9 transgenic plants, wherein, WT was the control plant, LT-2, L3-7 and L4-26 were three groups of CRF9 transgenic plants. It can be seen from FIG. 8 that the expression level of CRF9 in the CRF9 transgenic plants is significantly higher than that in the control group. It can be seen that the screened CRF9 transgenic plants are positive plants, which can highly express CRF9.

Figures 9, 10:
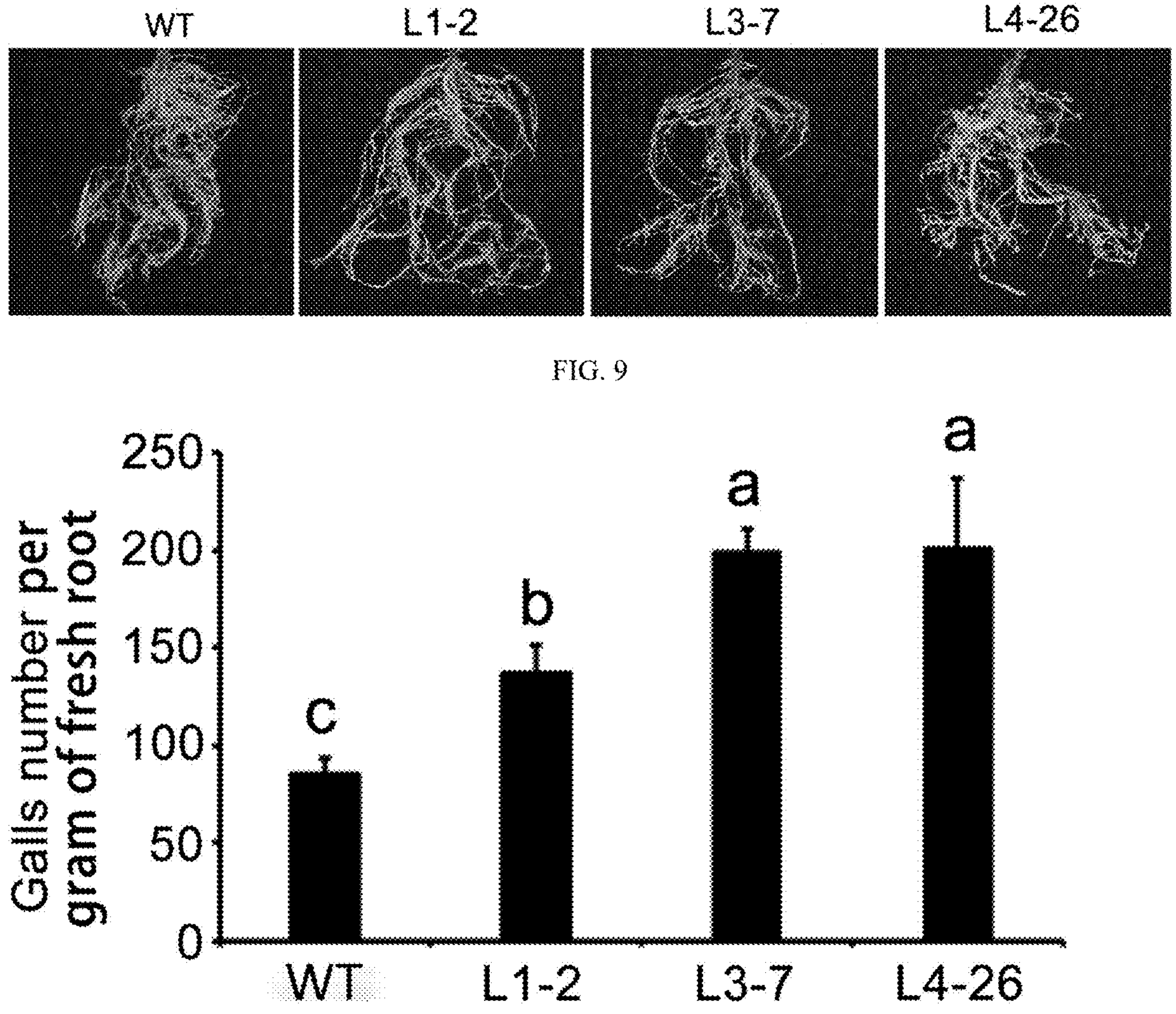
FIG. 9 is a root system diagram of CRF9 transgenic plants after root-knot nematode infection in embodiment 7 of the present invention.
FIG. 10 is a statistical diagram of the number of root nodes in CRF9 transgenic plants after root-knot nematode infection in embodiment 7 of the present invention.

FIG. 9 shows the root conditions of miRNA miRcn1 transgenic plants infected with root-knot nematodes, wherein, WT was the control plant, LT-2, L3-7 and L4-26 were three groups of CRF9 transgenic plants. It can be seen from FIG. 9 that the number of root knots of LT-2, L3-7 and L4-26 were significantly higher than that of the control group. It can be seen that CRF9 can promote the infection of root-knot nematodes.

FIG. 10 is a graph showing the number of root knots of CRF9 transgenic plants infected with root knot nematodes, wherein, WT was the control plant, LT-2, L3-7 and L4-26 were three groups of CRF9 transgenic plants. It can be seen from FIG. 10 that the number of root knots of LT-2, L3-7 and L4-26 were significantly higher than that of the control group. It can be seen that crf9 can promote the infection of root-knot nematodes.

Embodiment 8

8.1 Construction of CRF9-Silenced Plants

Construction of gene silenced plants by using VIGS technology. Using tomato cDNA as a template, primers were designed according to the CDS region of tomato CRF9, and the fragment was ligated to the pTRV2 vector by selecting appropriate restriction sites. pTRVT, pTRV2, pTRV2-PDS, pTRV2-CRF9 were transformed into *Agrobacterium* GV3101 respectively. The *Agrobacterium* containing the above plasmids were activated overnight. The *Agrobacterium* were transferred to LB medium containing 50 mg/L Km, 25 mg/L Rif, 10 mM MES and 20 μM acetosyringone and cultured overnight. The bacterial was collected by centrifugation, and the pellet was resuspended in buffer (10 mM $MgCl_2$, 10 mM MES, 200 μM acetosyringone), wherein, OD600 was about 0.8-1.0. The *Agrobacterium* suspension containing pTRV2 and the target fragment and the *Agrobacterium* suspension containing pTRV1 were mixed and co-injected into tomato at a ratio of 1:1 to obtain target gene silenced plants. After 3 weeks, the leaves and roots can be used for further experiments. The silencing of target genes in VIGS plants was verified by qRT-PCR.

8.2 Root-Knot Nematodes Infect CRF9-Silenced Plants

The root knot nematode second instar larvae were obtained according to Embodiment 7. 500 heads of J2 were inoculated in the rhizosphere of the silent plants obtained above. Tomato root tissues were collected 4 weeks after inoculation, and the number of root knots per plant and the number of root knots per unit mass were counted to observe the resistance of the silent plants to root knot nematodes. The results are shown in FIG. 11 and FIG. 12.

Figure 11:
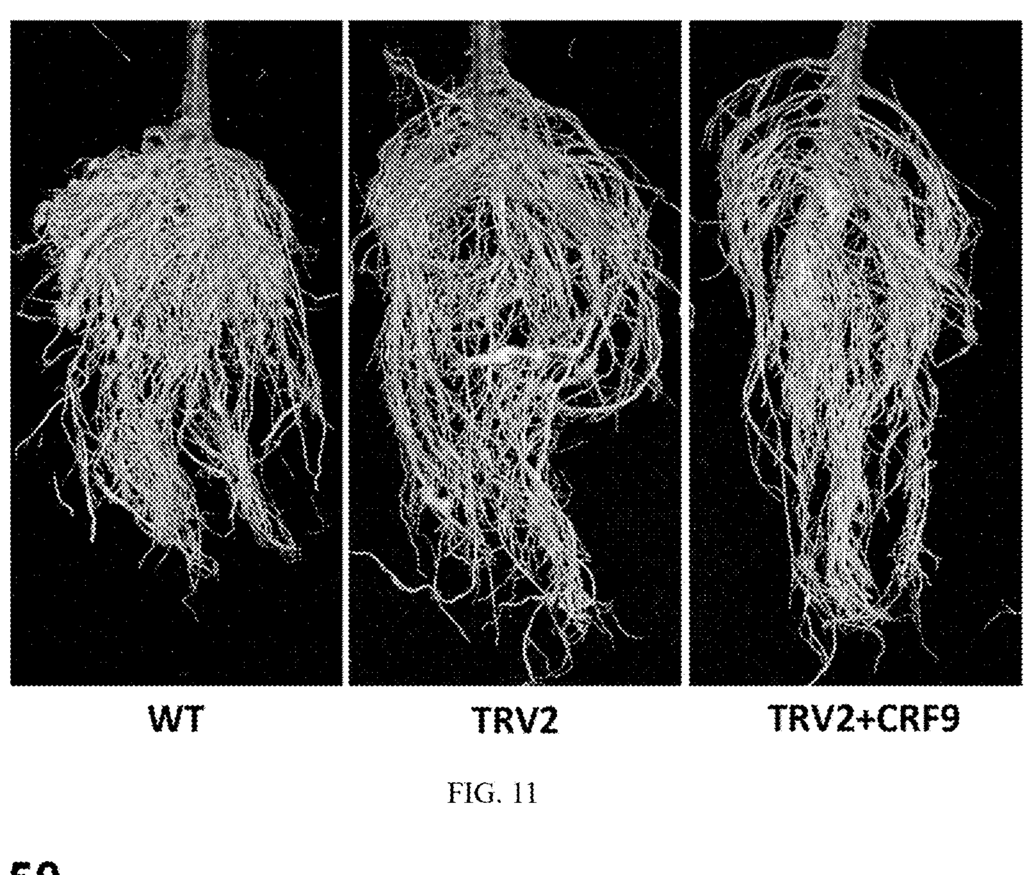
FIG. 11 is a root system diagram of three groups of plants: control, TRV2 vector-silenced plants, TRV2 vector and CRF9-silenced plants, in embodiment 8 of the present invention.

FIG. 11 is the root diagram of the three groups of plants of the control group, the TRV2 empty vector plants, and the CRF9-silenced plants. It can be seen from FIG. 11 that the number of root knots in CRF9-silenced plants was significantly less than that in the control and TRV2 groups.

Figure 12:
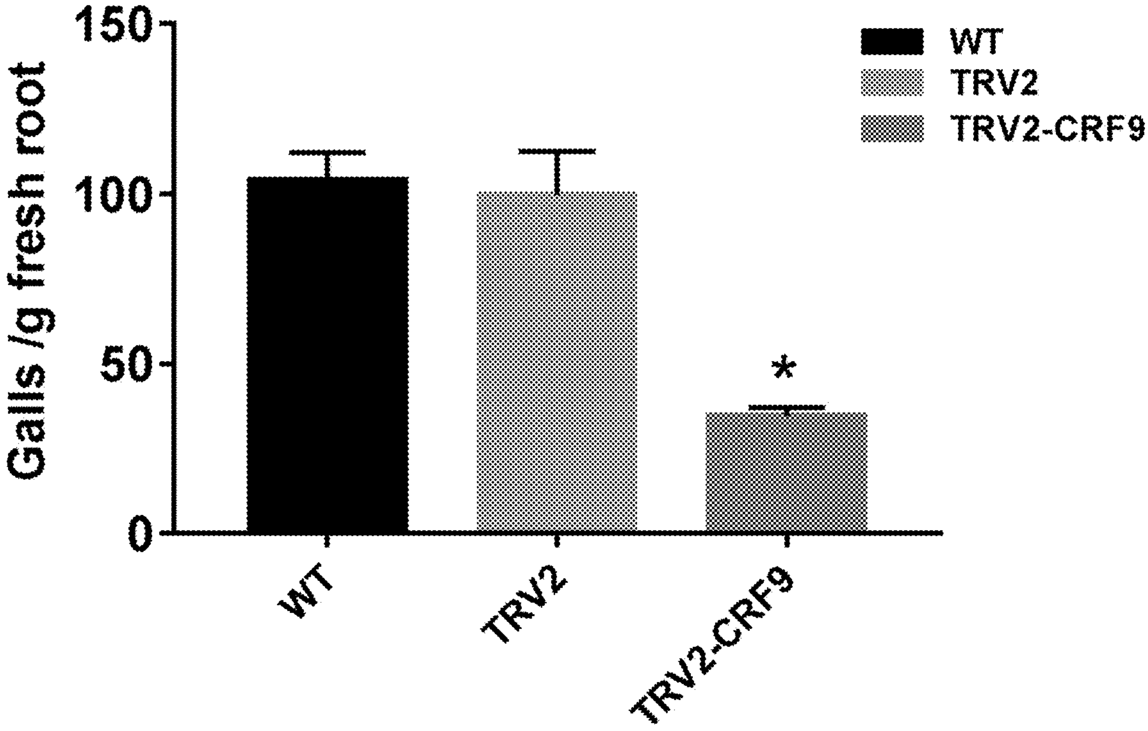
FIG. 12 shows the statistical graph of the number of root nodes of the three groups of plants of the control, TRV2 vector-silenced plants, TRV2 vector and CRF9-silenced plants in embodiment 8 of the present invention.

FIG. 12 is a statistical diagram of root knots of three groups of plants of control group, TRV2 empty vector plants, and CRF9-silenced plants. It can be seen from FIG. 12 that there is no difference in the root knots of the control group and the TRV2 empty vector plants, while the root knots of the CRF9-silenced plants are significantly reduced. It can be seen that silencing of TRV2 empty vector has almost no effect on root knot nematode infection, while CRF9-silencing can inhibit root knot nematode infection.

The above embodiments are merely illustrative of several implementation manners of the present disclosure, and the description thereof is more specific and detailed, but is not to be construed as a limitation to the patentable scope of the present disclosure. It should be pointed out that several variations and improvements can be made by those of ordinary skill in the art without departing from the conception of the present disclosure, but such variations and improvements should fall within the protection scope of the present disclosure. Therefore, the protection scope of the patent of the present disclosure should be subject to the appended claims.

What is claimed is:

1. An application of an isolated miRNA in the prevention and/or control of root-knot nematode disease, wherein the isolated miRNA is miRcn1 shown in SEQ ID NO: 1; and, miRcn1 inhibits the expression of CRF9 gene, wherein the prevention and/or treatment of root-knot nematode disease comprises:

preventing and/or treating root-knot nematode infections occurring in plant; or enhancing resistance to root-knot nematodes of plant;

wherein the plant is the tomato plant overexpressing CRF9 gene.

2. A method of producing transgenic plant, wherein the method includes the following steps:

S1, transforming an isolated miRNA into plant callus; and,

S2, regenerating a transgenic plant from the plant callus obtained in S1;

wherein the isolated miRNA is miRcn1 shown in SEQ ID NO: 1; miRcn1 inhibits the expression of CRF9 gene; and, the plant is a tomato plant.

* * * * *

SEQUENCE LISTING

```
<160> NUMBER OF SEQ ID NOS: 14

<210> SEQ ID NO 1
<211> LENGTH: 22
<212> TYPE: DNA
<213> ORGANISM: artificial sequence
<220> FEATURE:
<223> OTHER INFORMATION: synthetic construct

<400> SEQUENCE: 1

taacttcgtc tagctcgcct tc                                              22


<210> SEQ ID NO 2
<211> LENGTH: 41
<212> TYPE: DNA
<213> ORGANISM: artificial sequence
<220> FEATURE:
<223> OTHER INFORMATION: synthetic construct

<400> SEQUENCE: 2

gataacttcg tctagctcgc cttctctctc ttttgtattc c                         41


<210> SEQ ID NO 3
<211> LENGTH: 41
<212> TYPE: DNA
<213> ORGANISM: artificial sequence
<220> FEATURE:
<223> OTHER INFORMATION: synthetic construct

<400> SEQUENCE: 3

gagaaggcga gctagacgaa gttatcaaag agaatcaatg a                         41


<210> SEQ ID NO 4
<211> LENGTH: 41
<212> TYPE: DNA
```

<213> ORGANISM: artificial sequence
<220> FEATURE:
<223> OTHER INFORMATION: synthetic construct

<400> SEQUENCE: 4
gagacggcga gctagtcgaa gttatcacag gtcgtgatat g 41

<210> SEQ ID NO 5
<211> LENGTH: 41
<212> TYPE: DNA
<213> ORGANISM: artificial sequence
<220> FEATURE:
<223> OTHER INFORMATION: synthetic construct

<400> SEQUENCE: 5
gataacttcg actagctcgc cgtctctaca tatatattcc t 41

<210> SEQ ID NO 6
<211> LENGTH: 25
<212> TYPE: DNA
<213> ORGANISM: artificial sequence
<220> FEATURE:
<223> OTHER INFORMATION: synthetic construct

<400> SEQUENCE: 6
ctgcaaggcg attaagttgg gtaac 25

<210> SEQ ID NO 7
<211> LENGTH: 28
<212> TYPE: DNA
<213> ORGANISM: artificial sequence
<220> FEATURE:
<223> OTHER INFORMATION: synthetic construct

<400> SEQUENCE: 7
gcggataaca atttcacaca ggaaacag 28

<210> SEQ ID NO 8
<211> LENGTH: 29
<212> TYPE: DNA
<213> ORGANISM: artificial sequence
<220> FEATURE:
<223> OTHER INFORMATION: synthetic construct

<400> SEQUENCE: 8
ccggaattca tggatggttg cattagttc 29

<210> SEQ ID NO 9
<211> LENGTH: 29
<212> TYPE: DNA
<213> ORGANISM: artificial sequence
<220> FEATURE:
<223> OTHER INFORMATION: synthetic construct

<400> SEQUENCE: 9
cgcggatcct tataccaaaa ctgcatcta 29

<210> SEQ ID NO 10
<211> LENGTH: 1158
<212> TYPE: DNA
<213> ORGANISM: artificial sequence
<220> FEATURE:
<223> OTHER INFORMATION: synthetic construct

<400> SEQUENCE: 10
atggatggtt gcattagttc agtgaggaaa gttcgcatag tttatgatga tcctgatgct 60

```
acggactctg agagcgatga tgatcagaat gctgctcgtt tcgataaaaa tgtgaacaga    120

atcaagcgtg ttgttaagga aattgttatt cctgttgttt catgggagaa tgattttaaa    180

aaatgttcta aacttgataa cattaggatt aaagattcca agaagattca tgaaaataag    240

aaggtgcagc taaaatcgac cgcgttgcct aaaggagtta ggatgaggaa atgggggaaa    300

tatgcagctg agatcagaga tccctcgcag gggaaaagaa tatggttagg gacttttgag    360

actgtggagg cggcttcaca agcatacgag gcaaagaggg ctgaatttga taggattatt    420

tcattgggga agggtaagaa tttgagccct ggtcctgctg agtgttctat ggcgtgtacg    480

tctcatccta caaatgggaa aaatcgtgtg tactcacacc cttccccgtc ttcggtgcta    540

gatgtcccca catcatcagc tgctgccccg gttgagtcca atgaaaatct aacgagagat    600

atggctcgaa tgccagattc aggttctgaa gattttagct tgagttttga ggaccaaatg    660

cttcatgaat ttatcaaaca aagacagggc atttcagaat tgatcgaaca tcctttgata    720

gaacaaggct cgatcagcaa tagcgttatg gagatgactg aagtgaatat caggaagaaa    780

acgaaagcca gacaaccaac gatagcaagt tgtaaaatat tgacaaaggg aactgaggac    840

tacagtaatg acaagtccat tttcagtgta ttaaacgagc ctacaatcat gtctcctatt    900

catacagagc tgcttcactt gaacatcgag gaaacagcag ttacggggaa tagcttgaaa    960

cttctaggct ttgatgacaa tgctttattt gataaagata tatcacaatt atttgatcca   1020

tatgcagatg ctatatgctt ggacaacact tttcaatgct gtgatggttg gaatgagtgt   1080

gtttattgca aaattttcaa agatgaagtc gacctagatg aagttgactt aagatggtta   1140

gatgcagttt tggtataa                                                 1158
```

<210> SEQ ID NO 11
<211> LENGTH: 20
<212> TYPE: DNA
<213> ORGANISM: artificial sequence
<220> FEATURE:
<223> OTHER INFORMATION: synthetic construct

<400> SEQUENCE: 11

```
ctaacagaac tcgccgtgaa                                                 20
```

<210> SEQ ID NO 12
<211> LENGTH: 20
<212> TYPE: DNA
<213> ORGANISM: artificial sequence
<220> FEATURE:
<223> OTHER INFORMATION: synthetic construct

<400> SEQUENCE: 12

```
catggcgatg ccttaaataa                                                 20
```

<210> SEQ ID NO 13
<211> LENGTH: 20
<212> TYPE: DNA
<213> ORGANISM: artificial sequence
<220> FEATURE:
<223> OTHER INFORMATION: synthetic construct

<400> SEQUENCE: 13

```
acgccataga acactcagca                                                 20
```

<210> SEQ ID NO 14
<211> LENGTH: 432
<212> TYPE: DNA

-continued

```
<213> ORGANISM: artificial sequence
<220> FEATURE:
<223> OTHER INFORMATION: synthetic construct

<400> SEQUENCE: 14

gaattcctgc agccccaaac acacgctcgg acgcatatta cacatgttca tacacttaat     60

actcgctgtt ttgaattgat gttttaggaa tatatatgta gagacggcga gctagtcgaa    120

gttatcacag gtcgtgatat gattcaatta gcttccgact cattcatcca aataccgagt    180

cgccaaaatt caaactagac tcgttaaatg aatgaatgat gcggtagaca aattggatca    240

ttgattctct ttgataactt cgtctagctc gccttctctc tcttttgtat tccaattttc    300

ttgattaatc tttcctgcac aaaaacatgc ttgatccact aagtgacata tatgctgcct    360

tcgtatatat agttctggta aaattaacat tttgggttta tctttattta aggcatcgcc    420

atggggggat cc                                                        432
```